(12) United States Patent
Lin et al.

(10) Patent No.: US 12,702,505 B2
(45) Date of Patent: Aug. 11, 2026

(54) ROBOT-ASSISTED AUTOMATIC INTRODUCTION METHOD AND DEVICE FOR TROCAR

(71) Applicant: GUANGZHOU OCULOTRONICS MEDICAL INSTRUMENT CO., LTD., Guangzhou (CN)

(72) Inventors: Shengzhi Lin, Guangzhou (CN); Pisong Yan, Guangzhou (CN)

(73) Assignee: GUANGZHOU OCULOTRONICS MEDICAL INSTRUMENT CO., LTD., Guangzhou (CN)

( * ) Notice: Subject to any disclaimer, the term of this patent is extended or adjusted under 35 U.S.C. 154(b) by 78 days.

(21) Appl. No.: 18/721,882

(22) PCT Filed: Nov. 24, 2022

(86) PCT No.: PCT/CN2022/134016
§ 371 (c)(1),
(2) Date: Jun. 20, 2024

(87) PCT Pub. No.: WO2023/116333
PCT Pub. Date: Jun. 29, 2023

(65) Prior Publication Data

US 2025/0064537 A1 Feb. 27, 2025

(30) Foreign Application Priority Data

Dec. 21, 2021 (CN) ........................ 202111577523.9

(51) Int. Cl.
*A61B 34/32* (2016.01)
*A61B 17/34* (2006.01)
(Continued)

(52) U.S. Cl.
CPC .......... *A61B 34/32* (2016.02); *A61B 17/3403* (2013.01); *G06T 7/70* (2017.01);
(Continued)

(58) Field of Classification Search
CPC ................ A61B 34/32; A61B 17/3403; A61B 2034/2065; A61B 34/30; A61B 17/34;
(Continued)

(56) References Cited

U.S. PATENT DOCUMENTS

2021/0059857 A1 3/2021 Voigt et al.
2021/0128260 A1 5/2021 Gonenc et al.
2021/0290311 A1 9/2021 Fuerst et al.

FOREIGN PATENT DOCUMENTS

CN 102905642 A 1/2013
CN 113538522 A 10/2021
(Continued)

*Primary Examiner* — Elizabeth Houston
(74) *Attorney, Agent, or Firm* — Bayramoglu Law Offices LLC

(57) ABSTRACT

A robot-assisted automatic introduction method and device for a trocar are provided. The robot-assisted automatic introduction method includes: acquiring a dataset of the trocar, and training through a preset U-Net to acquire a first model; detecting, by the first model, a position of the trocar in a target image, and outputting position information of the trocar that meets a preset condition; parameterizing, according to the position information of the trocar that meets the preset condition, a rotation angle of the trocar, and acquiring a rotation matrix of the trocar; and acquiring, according to the rotation matrix of the trocar, an orientation of the trocar, and controlling, according to the orientation of the trocar, an instrument at an end of the robot to introduce the trocar.

15 Claims, 2 Drawing Sheets

(51) Int. Cl.
*A61B 34/20* (2016.01)
*G06T 7/70* (2017.01)
*G16H 40/63* (2018.01)

(52) U.S. Cl.
CPC ...... *G16H 40/63* (2018.01); *A61B 2034/2065* (2016.02); *G06T 2207/20081* (2013.01); *G06T 2207/20084* (2013.01); *G06T 2207/30004* (2013.01)

(58) Field of Classification Search
CPC .......... A61B 90/361; A61B 2034/2055; A61B 2034/301; A61B 34/10; A61B 34/20; A61B 2034/101
See application file for complete search history.

(56) References Cited

FOREIGN PATENT DOCUMENTS

| | | | |
|---|---|---|---|
| CN | 114159166 | A | 3/2022 |
| WO | 2012034886 | A1 | 3/2012 |

ROBOT-ASSISTED AUTOMATIC INTRODUCTION METHOD AND DEVICE FOR TROCAR

CROSS-REFERENCE TO TILE RELATED APPLICATIONS

This application is the national phase entry of International Application No. PCT/CN2022/134016, filed on Nov. 24, 2022, which is based upon and claims priority to Chinese Patent Application No. 202111577523.9, filed on Dec. 21, 2021, the entire contents of which are incorporated herein by reference.

TECHNICAL FIELD

The present disclosure relates to the field of robot control, and in particular to a robot-assisted automatic introduction method and device for a trocar.

BACKGROUND

Automatic navigation is a crucial part of robot-assisted surgery. At present, in the common automatic navigation technology, medical imaging data acquired by magnetic resonance imaging (MRI), computed tomography (CT) or other technique are processed through an image processing technique to generate a visual three-dimensional (3D) model. In this way, a preset movement path is provided for the robot. This offline modeling method has poor adaptability, and requires repeated modeling for different samples before surgery. It is only suitable for operations with poor visibility, and requires complete image data, putting forward high requirements for the image data.

SUMMARY

The present disclosure provides a robot-assisted automatic introduction method and device for a trocar. The present disclosure solves the technical problem of how to automatically determine the orientation of a trocar.

In order to solve the above technical problem, an embodiment of the present disclosure provides a robot-assisted automatic introduction method for a trocar, including:

acquiring a dataset of the trocar, and training through a preset U-Net to acquire a first model;

detecting, by the first model, a position of the trocar in a target image, and outputting position information of the trocar that meets a preset condition;

parameterizing, according to the position information of the trocar that meets the preset condition, a rotation angle of the trocar, and acquiring a rotation matrix of the trocar; and acquiring, according to the rotation matrix of the trocar, an orientation of the trocar, and controlling, according to the orientation of the trocar, an instrument at an end of the robot to introduce the trocar.

In a preferred solution, the outputting position information of the trocar that meets a preset condition specifically includes:

outputting position information of the trocar that meets the following condition:

$$pred(x, y) \geq 0.8 * \max(pred);$$

where, (x,y) denotes a pixel position of the trocar; pred (x,y) denotes a confidence of the pixel position (x,y) being classified as trocar; and max(pred) denotes an overall maximum value of an image output by the U-Net.

In a preferred solution, before parameterizing a rotation angle of the trocar, the robot-assisted automatic introduction method further includes: processing the position information of the trocar that meets the preset condition, specifically:

calculating a median value of the position information in every seven consecutive image frames, calculating a Euclidean distance between the median value and the position information in each of the seven consecutive image frames, and averaging position information with the Euclidean distance less than or equal to a quarter of a standard deviation to acquire final position information of the trocar.

In a preferred solution, the acquiring a rotation matrix of the trocar specifically includes:

acquiring a rotation matrix $R_z$ of the trocar in a z-direction and a rotation matrix $R_y$ of the trocar in a y-direction; and calculating a six-dimensional rotation matrix R of the trocar:

$$R = [R1 \quad R2 \quad R3], \begin{cases} R1 = \phi(R_Z) \\ R3 = \phi(R1 \times R_Y); \\ R2 = R3 \times R1 \end{cases}$$

where, R1, R2, and R3 denote columns of the six-dimensional rotation matrix R.

In a preferred solution, the acquiring, according to the rotation matrix of the trocar, an orientation of the trocar specifically includes:

acquiring a true value $$R_Z^{pred}$$

of the trocar in the dataset, and calculating the orientation of the trocar according to the rotation matrix $$R_Z^{gt}$$

of the trocar:

$$\Delta\theta = \text{across}\left(R_Z^{gt} \cdot R_Z^{pred}\right);$$

where, the orientation of the trocar is expressed by an angle $\Delta\theta$ between the rotation matrix $$R_Z^{gt}$$

of the trocar and the true value $$R_Z^{pred}$$

of the trocar.

Correspondingly, the present disclosure further provides a robot-assisted automatic introduction device for a trocar, including a training module, a detection module, a rotation matrix module, and an introduction module, where the training module is configured to acquire a dataset of the trocar, and train through a preset U-Net to acquire a first model;

the detection module is configured to detect, by the first model, a position of the trocar in a target image, and output position information of the trocar that meets a preset condition;

the rotation matrix module is configured to parameterize, according to the position information of the trocar that meets the preset condition, a rotation angle of the trocar, and acquire a rotation matrix of the trocar; and the introduction module is configured to acquire, according to the rotation matrix of the trocar, an orientation of the trocar, and control, according to the orientation of the trocar, an instrument at an end of the robot to introduce the trocar.

In a preferred solution, the detection module is configured to output position information of the trocar that meets a preset condition; and specifically:

the detection module is configured to output position information of the trocar that meets the following condition:

$$pred(x, y) \geq 0.8 * \max(pred);$$

where, (x,y) denotes a pixel position of the trocar; pred (x,y) denotes a confidence of the pixel position (x,y) being classified as trocar; and max(pred) denotes an overall maximum value of an image output by the U-Net.

In a preferred solution, the robot-assisted automatic introduction device further includes a screening module configured to process the position information of the trocar that meets the preset condition before the rotation matrix module parameterizes the rotation angle of the trocar; and specifically:

the screening module is configured to calculate a median value of the position information in every seven consecutive image frames, calculate a Euclidean distance between the median value and the position information in each of the seven consecutive image frames, and average position information with the Euclidean distance less than or equal to a quarter of a standard deviation to acquire final position information of the trocar.

In a preferred solution, the rotation matrix module is configured to acquire a rotation matrix of the trocar; and specifically:

the rotation matrix module is configured to acquire a rotation matrix $R_z$ of the trocar in a z-direction and a rotation matrix $R_y$ of the trocar in a y-direction, and calculate a six-dimensional rotation matrix R of the trocar;

$$R = [R1 \quad R2 \quad R3], \begin{cases} R1 = \phi(R_Z) \\ R3 = \phi(R1 \times R_Y); \\ R2 = R3 \times R1 \end{cases}$$

where, R1, R2, and R3 denote columns of the six-dimensional rotation matrix R.

In a preferred solution, the introduction module is configured to acquire, according to the rotation matrix of the trocar, an orientation of the trocar; and specifically:

the introduction module is configured to acquire a true value $$R_Z^{pred}$$

of the trocar in the dataset, and calculate the orientation of the trocar according to the rotation matrix $$R_Z^{gt}$$

of the trocar:

$$\Delta\theta = \text{across}\left(R_Z^{gt} \cdot R_Z^{pred}\right);$$

where, the orientation of the trocar is expressed by an angle $\Delta\theta$ between the rotation matrix $$R_Z^{gt}$$

of the trocar and the true value $$R_Z^{pred}$$

of the trocar.

Compared with the prior art, the embodiments of the present disclosure have following beneficial effects:

The embodiments of the present disclosure provide a robot-assisted automatic introduction method and device for a trocar. The robot-assisted automatic introduction method includes: acquiring a dataset of the trocar, and training through a preset U-Net to acquire a first model; detecting, by the first model, a position of the trocar in a target image, and outputting position information of the trocar that meets a preset condition; parameterizing, according to the position information of the trocar that meets the preset condition, a rotation angle of the trocar, and acquiring a rotation matrix of the trocar; and acquiring, according to the rotation matrix of the trocar, an orientation of the trocar, and controlling, according to the orientation of the trocar, an instrument at an end of the robot to introduce the trocar. Compared with the prior art, the present disclosure detects the position of the trocar and acquires the orientation of the trocar through the U-Net. The present disclosure can accurately control the instrument at the end of the robot to introduce the trocar, and automatically determine the orientation of the trocar, adapting to in-vivo operations with poor visibility.

DETAILED DESCRIPTION OF THE EMBODIMENTS

The technical solutions of the embodiments of the present disclosure are clearly and completely described below with reference to the drawings. Apparently, the described embodiments are merely a part rather than all of the embodiments of the present disclosure. All other embodiments obtained by those of ordinary skill in the art based on the embodiments of the present disclosure without creative efforts should fall within the protection scope of the present disclosure.

Embodiment 1

Figure 1:
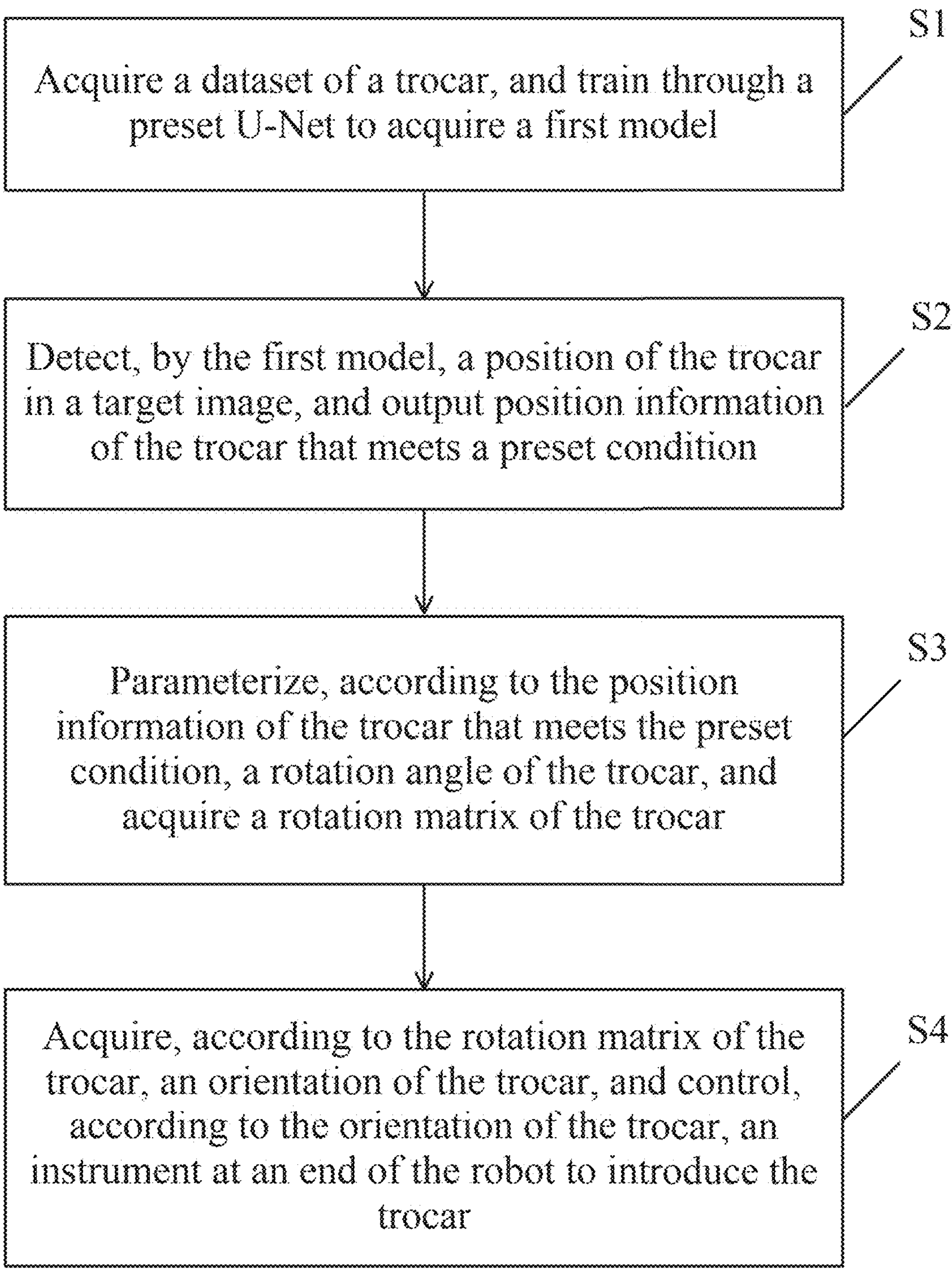
FIG. 1 is a flowchart of a robot-assisted automatic introduction method for a trocar according to an embodiment of the present disclosure.

FIG. 1 is a flowchart of a robot-assisted automatic introduction method for a trocar provided by an embodiment of the present disclosure. Referring to FIG. 1, the method includes steps S1 to S4. This embodiment adopts a five-degree-of-freedom series/parallel ophthalmic surgical robot and a multifunctional welding magnifier camera. The series/parallel ophthalmic surgical robot includes a first joint and a second joint for two-axis translation and rotation and a sliding rail joint for z-axis motion of an end effector. The first joint is provided with a first linear motor and a second linear motor, while the second joint is provided with a third linear motor and a fourth linear motor. The sliding rail joint is provided with a fifth linear motor. The multifunctional welding magnifier camera is rigidly provided on a syringe at an end of a robot in a preset direction through a three-dimensional (3D) printing bracket.

S1. A dataset of the trocar is acquired, and training is performed through a preset U-Net to acquire a first model.

In this embodiment, the multifunctional welding magnifier camera provided on the robot is configured to capture image frames, acquire red, green, and blue (RGB) images of the trocar, and generate a dataset of the trocar. The dataset includes no less than 2,000 images, which include real ground information of the trocar in an image coordinate system and a three-dimensional position of the trocar relative to the camera in a virtual scene. The U-Net with Resnet34 as a core feature extractor is selected for training to form an optimal model. The U-Net first pre-trains with the dataset of the trocar, and then fine-tunes with a dataset of the trocar after marking to acquire the first model. A last network layer of the U-Net uses a sigmoid activation function and a binary cross entropy loss function.

S2. A position of the trocar in a target image is detected by the first model, and position information of the trocar that meets a preset condition is output.

In this embodiment, final image coordinates of the position of the trocar after each frame processing are acquired through the first model. For this purpose, all pixel positions (x,y) that meet the condition in the output of the U-Net are taken as candidate positions of the trocar, that is, the position information of the trocar that meets the preset condition. Specifically:

Position information of the trocar is output, which meets the following condition:

$$pred(x, y) \geq 0.8 * \max(pred);$$

where, (x,y) denotes a pixel position of the trocar; pred (x,y) denotes a confidence of the pixel position (x,y) being classified as trocar; and max(pred) denotes an overall maximum value of an image output by the U-Net.

Further, the position information of the trocar that meets the preset condition is further processed. Specifically:

A median value of the position information in every seven consecutive image frames is calculated, a Euclidean distance between the median value and the position information in each of the seven consecutive image frames is calculated, position information with the Euclidean distance less than or equal to a quarter of a standard deviation is averaged, and final position information of the trocar is acquired. In this way, the processing results are robust.

S3. A rotation angle of the trocar is parameterized according to the position information of the trocar that meets the preset condition, and a rotation matrix of the trocar is acquired.

Specifically, in this embodiment, the rotation matrix of the trocar is acquired in the following manner.

The rotation angle of the trocar is parameterized. A coordinate system is established for the trocar by taking a center of a cross-section of the trocar as an origin, the cross-section of the trocar as an XY plane of the coordinate system, and a normal vector of the cross-section as the z-axis.

A six-dimensional rotation matrix $R_{6d}$ of the trocar is expressed as follows:

$$R_{6d} = [R_Z | R_Y];$$

where, $R_z$ denotes a rotation matrix of the trocar in a z-direction, and $R_y$ denotes a rotation matrix of the trocar in a y-direction.

The rotation matrix $R_z$ of the trocar in the z-direction and the rotation matrix $R_y$ of the trocar in the y-direction are acquired; and the six-dimensional rotation matrix R of the trocar is calculated, R being a unit and orthogonal rotation matrix.

$$R = [R1 \;\; R2 \;\; R3], \begin{cases} R1 = \phi(R_Z) \\ R3 = \phi(R1 \times R_Y); \\ R2 = R3 \times R1 \end{cases}$$

where, R1, R2, and R3 denote columns of the six-dimensional rotation matrix R; and q) denotes a vector normalization operation.

S4. According to the rotation matrix of the trocar, an orientation of the trocar is acquired, and according to the orientation of the trocar, an instrument at an end of the robot is controlled to introduce the trocar.

Specifically, based on the image frame, a normal vector of the cross-section closest to the trocar on the current image plane is estimated to determine the appropriate position of the target trocar. For an input image extracted from a region of interest (ROT) centered on the trocar, it is converted into a feature through a Resnet34-based feature extractor, and is expressed as a six-dimensional rotation matrix through a fully connected layer. True value $$R_Z^{pred}$$

of the trocar in the dataset is acquired, and the orientation of the trocar is calculated according to the rotation matrix $$R_Z^{gt}$$

of the trocar:

$$\Delta\theta = \text{across}(R_Z^{gt} \cdot R_Z^{pred});$$

where, the orientation of the trocar is expressed by angle $\Delta\theta$ between the rotation matrix $$R_Z^{gt}$$

of the trocar and the true value $$R_Z^{pred}$$

of the trocar.

Since the trocar is symmetric along the z-axis, loss function L is designed to avoid punishing the network due to irrelevant rotation around the z-axis of the trocar. Therefore, a mean square error (MSE) is proportional to a cosine distance of $\Delta\theta$, and the loss function $L_{rotation}$ is specifically expressed as follows:

$$L_{rotation} = MSE(R_Z^{gt} \cdot R_Z^{pred});$$

For determined position data of the trocar, when the end of the robot is placed within an accessible distance of the trocar (such that the robot can complete the operation within a maximum working range), a two-stage step-by-step alignment method is used to align the direction of the instrument at the end of the robot with the direction of the trocar. Through translation, the XY of an end of the instrument at the end of the robot is aligned with the trocar so as to compensate for minor intraoperative movement of the trocar. The end of the instrument is always maintained on a connecting line of the trocar and approaches the trocar at an adaptive speed to complete introduction.

In this embodiment, preferably, the trocar is provided with an infrared reflector, and the miniature camera is provided with an infrared detector to assist in detecting the position of the trocar and helping to determine the position range of the trocar. In addition, it should be noted that the robot-assisted automatic introduction method for a trocar described in this embodiment only demonstrates its application in ophthalmic surgery, but this is only an example. The robot-assisted automatic introduction method can also be applied to other types of minimally invasive robotic surgeries.

Figure 2:
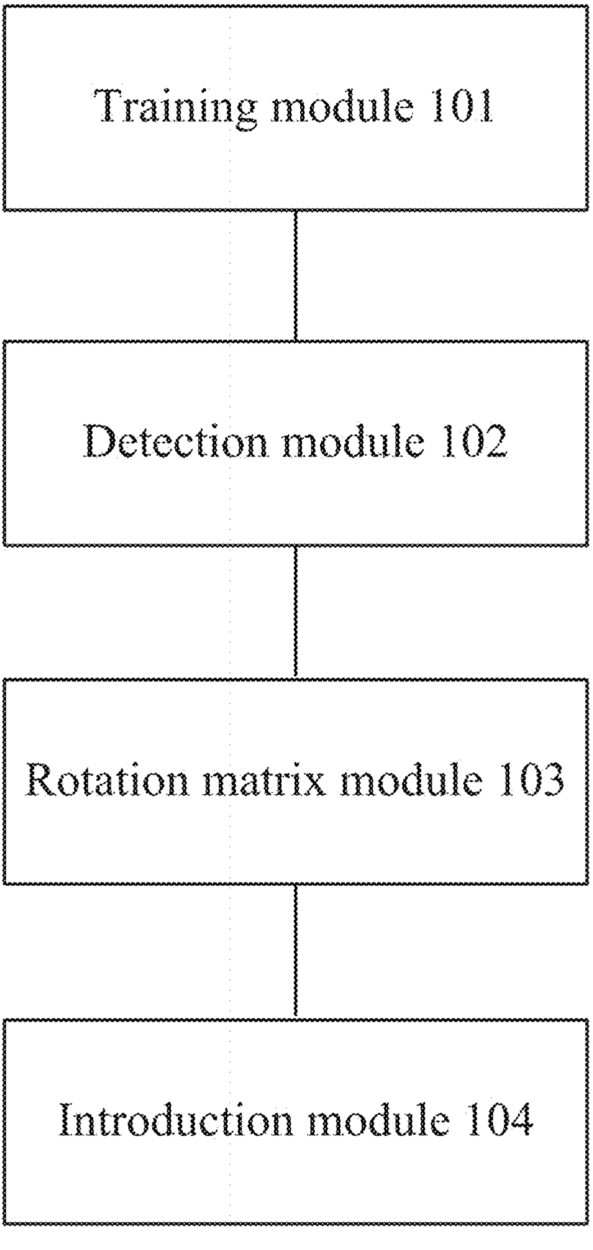
FIG. 2 is a block diagram of a robot-assisted automatic introduction device for a trocar according to an embodiment of the present disclosure.

Correspondingly, the present disclosure further provides a robot-assisted automatic introduction device for a trocar. Referring to FIG. 2, the robot-assisted automatic introduction device includes training module 101, detection module 102, rotation matrix module 103, and introduction module 104.

The training module 101 is configured to acquire a dataset of the trocar, and train through a preset U-Net to acquire a first model.

The detection module 102 is configured to detect, by the first model, a position of the trocar in a target image, and output position information of the trocar that meets a preset condition.

The rotation matrix module 103 is configured to parameterize, according to the position information of the trocar that meets the preset condition, a rotation angle of the trocar, and acquire a rotation matrix of the trocar.

The introduction module 104 is configured to acquire, according to the rotation matrix of the trocar, an orientation of the trocar, and control, according to the orientation of the trocar, an instrument at an end of the robot to introduce the trocar.

In this embodiment, the detection module 102 is configured to output position information of the trocar that meets a preset condition. Specifically:

The detection module 102 is configured to output position information of the trocar that meets the following condition:

$$pred(x, y) \geq 0.8 * \max(pred);$$

where, (x,y) denotes a pixel position of the trocar; pred (x,y) denotes a confidence of the pixel position (x,y) being classified as trocar; and max(pred) denotes an overall maximum value of an image output by the U-Net.

In this embodiment, the robot-assisted automatic introduction device further includes a screening module configured to process the position information of the trocar that meets the preset condition before the rotation matrix module 103 parameterizes the rotation angle of the trocar. Specifically:

The screening module is configured to calculate a median value of the position information in every seven consecutive image frames, calculate a Euclidean distance between the median value and the position information in each of the seven consecutive image frames, and average position information with the Euclidean distance less than or equal to a quarter of a standard deviation to acquire final position information of the trocar.

In this embodiment, the rotation matrix module 103 is configured to acquire a rotation matrix of the trocar. Specifically:

The rotation matrix module 103 is configured to acquire rotation matrix $R_z$ of the trocar in a z-direction and rotation matrix $R_y$ of the trocar in a y-direction, and calculate six-dimensional rotation matrix R of the trocar.

$$R = [R1 \quad R2 \quad R3], \begin{cases} R1 = \phi(R_Z) \\ R3 = \phi(R1 \times R_Y); \\ R2 = R3 \times R1 \end{cases}$$

where, R1, R2, and R3 denote columns of the six-dimensional rotation matrix R.

In this embodiment, the introduction module 104 is configured to acquire, according to the rotation matrix of the trocar, an orientation of the trocar. Specifically:

The introduction module 104 is configured to acquire true value $$R_Z^{pred}$$

of the trocar in the dataset, and calculate the orientation of the trocar according to the rotation matrix $$R_Z^{gt}$$

of the trocar:

$$\Delta\theta = \text{across}(R_Z^{gt} \cdot R_Z^{pred});$$

where, the orientation of the trocar is expressed by angle Δθ between the rotation matrix $$R_Z^{gt}$$

of the trocar and the true value $$R_Z^{pred}$$

of the trocar.

Compared with the prior art, the embodiments of the present disclosure have following beneficial effects:

The embodiments of the present disclosure provide a robot-assisted automatic introduction method and device for a trocar. The robot-assisted automatic introduction method includes: acquiring a dataset of the trocar, and training through a preset U-Net to acquire a first model; detecting, by the first model, a position of the trocar in a target image, and outputting position information of the trocar that meets a preset condition; parameterizing, according to the position information of the trocar that meets the preset condition, a rotation angle of the trocar, and acquiring a rotation matrix of the trocar; and acquiring, according to the rotation matrix of the trocar, an orientation of the trocar, and controlling, according to the orientation of the trocar, an instrument at an end of the robot to introduce the trocar. Compared with the prior art, the present disclosure detects the position of the trocar and acquires the orientation of the trocar through the U-Net. The present disclosure can accurately control the instrument at the end of the robot to introduce the trocar, and automatically determine the orientation of the trocar, adapting to in-vivo operations with poor visibility.

The objectives, technical solutions, and beneficial effects of the present disclosure are further described in detail through the above specific embodiments. It should be understood that the above are merely some specific embodiments of the present disclosure, but are not intended to limit the protection scope of the present disclosure. It should be particularly noted that, any modifications, equivalent substitutions, improvements, and the like made by those skilled in the art within the spirit and principle of the present disclosure should be included within the protection scope of the present disclosure.

What is claimed is:

1. A robot-assisted automatic introduction method for a trocar, comprising:

acquiring a dataset of the trocar, and training through a preset U-Net to acquire a first model;

detecting, by the first model, a position of the trocar in a target image, and outputting position information of the trocar that meets a preset condition;

parameterizing, according to the position information of the trocar that meets the preset condition, a rotation angle of the trocar, and acquiring a rotation matrix of the trocar; and acquiring, according to the rotation matrix of the trocar, an orientation of the trocar, and controlling, according to the orientation of the trocar, an instrument at an end of a robot to introduce the trocar;

wherein the step of outputting the position information of the trocar that meets the preset condition comprises:

outputting the position information of the trocar that meets the following condition:

$$pred(x, y) \geq 0.8 * \max(pred);$$

wherein (x,y) denotes a pixel position of the trocar; pred(x,y) denotes a confidence of the pixel position (x,y) being classified as the trocar; and max(pred) denotes an overall maximum value of an image output by the U-Net.

2. The robot-assisted automatic introduction method for the trocar according to claim 1, wherein the step of acquiring the rotation matrix of the trocar comprises:

acquiring a rotation matrix $R_z$ of the trocar in a z-direction and a rotation matrix $R_y$ of the trocar in a y-direction, and calculating a six-dimensional rotation matrix R of the trocar;

$$R = [\,R1 \quad R2 \quad R3\,], \begin{cases} R1 = \phi(R_Z) \\ R3 = \phi(R1 \times R_Y); \\ R2 = R3 \times R1 \end{cases}$$

wherein R1, R2, and R3 denote columns of the six-dimensional rotation matrix R.

3. The robot-assisted automatic introduction method for the trocar according to claim 2, wherein the step of acquiring, according to the rotation matrix of the trocar, the orientation of the trocar comprises:

acquiring a true value $$R_Z^{pred}$$

of the trocar in the dataset, and calculating the orientation of the trocar according to the rotation matrix $$R_Z^{gt}$$

of the trocar:

$$\Delta\theta = \text{across}(R_Z^{gt} \cdot R_Z^{pred});$$

wherein the orientation of the trocar is expressed by an angle Δθ between the rotation matrix $$R_Z^{gt}$$

of the trocar and the true value $$R_Z^{pred}$$

of the trocar.

4. The robot-assisted automatic introduction method for the trocar according to claim 2, wherein the step of acquiring, according to the rotation matrix of the trocar, the orientation of the trocar comprises:

acquiring a true value $$R_z^{pred}$$

of the trocar in the dataset, and calculating the orientation of the trocar according to the rotation matrix $$R_z^{gt}$$

of the trocar:

$$\Delta\theta = \text{across}\left(R_Z^{gt} \cdot R_Z^{pred}\right);$$

wherein the orientation of the trocar is expressed by an angle Δθ between the rotation matrix $$R_z^{gt}$$

of the trocar and the true value $$R_z^{pred}$$

of the trocar.

5. A robot-assisted automatic introduction method for a trocar, comprising:

acquiring a dataset of the trocar, and training through a preset U-Net to acquire a first model;

detecting, by the first model, a position of the trocar in a target image, and outputting position information of the trocar that meets a preset condition;

parameterizing, according to the position information of the trocar that meets the preset condition, a rotation angle of the trocar, and acquiring a rotation matrix of the trocar; and acquiring, according to the rotation matrix of the trocar, an orientation of the trocar, and controlling, according to the orientation of the trocar, an instrument at an end of a robot to introduce the trocar;

wherein before parameterizing the rotation angle of the trocar, the robot-assisted automatic introduction method further comprises: a step of processing the position information of the trocar that meets the preset condition, comprising:

calculating a median value of the position information in every seven consecutive image frames, calculating a Euclidean distance between the median value and the position information in each of the seven consecutive image frames, and averaging position information with the Euclidean distance less than or equal to a quarter of a standard deviation to acquire final position information of the trocar.

6. The robot-assisted automatic introduction method for the trocar according to claim 5, wherein the step of acquiring the rotation matrix of the trocar comprises:

acquiring a rotation matrix $R_z$ of the trocar in a z-direction and a rotation matrix $R_y$ of the trocar in a v-direction, and calculating a six-dimensional rotation matrix R of the trocar;

$$R = [\,R1 \quad R2 \quad R3\,], \begin{cases} R1 = \phi(R_Z) \\ R3 = \phi(R1 \times R_Y); \\ R2 = R3 \times R1 \end{cases}$$

wherein R1, R2, and R3 denote columns of the six-dimensional rotation matrix R.

7. The robot-assisted automatic introduction method for the trocar according to claim 6, wherein the step of acquiring, according to the rotation matrix of the trocar, the orientation of the trocar comprises:

acquiring a true value $$R_z^{pred}$$

of the trocar in the dataset, and calculating the orientation of the trocar according to the rotation matrix $$R_z^{gt}$$

of the trocar:

$$\Delta\theta = \text{across}\left(R_Z^{gt} \cdot R_Z^{pred}\right);$$

wherein the orientation of the trocar is expressed by an angle Δθ between the rotation matrix $$R_z^{gt}$$

of the trocar and the true value $$R_z^{pred}$$

of the trocar.

8. A robot-assisted automatic introduction device for a trocar, comprising a training module, a detection module, a rotation matrix module, and an introduction module, wherein the training module is configured to acquire a dataset of the trocar, and train through a preset U-Net to acquire a first model;

the detection module is configured to detect, by the first model, a position of the trocar in a target image, and output position information of the trocar that meets a preset condition;

the rotation matrix module is configured to parameterize, according to the position information of the trocar that meets the preset condition, a rotation angle of the trocar, and acquire a rotation matrix of the trocar; and the introduction module is configured to acquire, according to the rotation matrix of the trocar, an orientation of the trocar, and control, according to the orientation of the trocar, an instrument at an end of a robot to introduce the trocar;

wherein the detection module is configured to output the position information of the trocar that meets the preset condition, wherein the detection module is configured to output the position information of the trocar that meets the following condition:

$$pred(x, y) \geqslant 0.8^{*} \max(pred);$$

wherein (x,y) denotes a pixel position of the trocar; pred(x,y) denotes a confidence of the pixel position (x,y) being classified as the trocar; and max(pred) denotes an overall maximum value of an image output by the U-Net.

9. The robot-assisted automatic introduction device for the trocar according to claim 8, further comprising a screening module configured to process the position information of the trocar that meets the preset condition before the rotation matrix module parameterizes the rotation angle of the trocar, wherein the screening module is configured to calculate a median value of the position information in every seven consecutive image frames, calculate a Euclidean distance between the median value and the position information in each of the seven consecutive image frames, and average position information with the Euclidean distance less than or equal to a quarter of a standard deviation to acquire final position information of the trocar.

10. The robot-assisted automatic introduction device for the trocar according to claim 9, wherein the rotation matrix module is configured to acquire the rotation matrix of the trocar, wherein the rotation matrix module is configured to acquire a rotation matrix $R_z$ of the trocar in a z-direction and a rotation matrix $R_y$ of the trocar in a y-direction, and calculate a six-dimensional rotation matrix R of the trocar;

$$R = [R1 \ \ R2 \ \ R3], \begin{cases} R1 = \phi(R_Z) \\ R3 = \phi(R1 \times R_Y); \\ R2 = R3 \times R1 \end{cases}$$

wherein R1, R2, and R3 denote columns of the six-dimensional rotation matrix R.

11. The robot-assisted automatic introduction device for the trocar according to claim 10, wherein the introduction module is configured to acquire, according to the rotation matrix of the trocar, the orientation of the trocar, wherein the introduction module is configured to acquire a true value $$R_z^{pred}$$

of the trocar in the dataset, and calculate the orientation of the trocar according to the rotation matrix $$R_z^{gt}$$

of the trocar:

$$\Delta\theta = \text{across}(R_Z^{gt} \cdot R_Z^{pred});$$

wherein the orientation of the trocar is expressed by an angle Δθ between the rotation matrix $$R_z^{gt}$$

of the trocar and the true value $$R_z^{pred}$$

of the trocar.

12. The robot-assisted automatic introduction device for the trocar according to claim 8, wherein the rotation matrix module is configured to acquire the rotation matrix of the trocar, wherein the rotation matrix module is configured to acquire a rotation matrix $R_z$ of the trocar in a z-direction and a rotation matrix $R_y$ of the trocar in a y-direction, and calculate a six-dimensional rotation matrix R of the trocar;

$$R = [R1 \ \ R2 \ \ R3], \begin{cases} R1 = \phi(R_Z) \\ R3 = \phi(R1 \times R_Y); \\ R2 = R3 \times R1 \end{cases}$$

wherein R1, R2, and R3 denote columns of the six-dimensional rotation matrix R.

13. The robot-assisted automatic introduction device for the trocar according to claim 12, wherein the introduction module is configured to acquire, according to the rotation matrix of the trocar, the orientation of the trocar, wherein the introduction module is configured to acquire a true value $$R_Z^{pred}$$

of the trocar in the dataset, and calculate the orientation of the trocar according to the rotation matrix $$R_z^{gt}$$

of the trocar:

$$\Delta\theta = \text{across}(R_Z^{gt} \cdot R_Z^{pred});$$

wherein the orientation of the trocar is expressed by an angle Δθ between the rotation matrix $$R_z^{gt}$$

of the trocar and the true value $$R_z^{pred}$$

of the trocar.

14. The robot-assisted automatic introduction device for the trocar according to claim 8, wherein the rotation matrix module is configured to acquire the rotation matrix of the trocar, wherein the rotation matrix module is configured to acquire a rotation matrix $R_z$ of the trocar in a z-direction and a rotation matrix $R_y$ of the trocar in a y-direction, and calculate a six-dimensional rotation matrix R of the trocar;

$$R = [R1 \quad R2 \quad R3], \begin{cases} R1 = \phi(R_Z) \\ R3 = \phi(R1 \times R_Y); \\ R2 = R3 \times R1 \end{cases}$$

wherein R1, R2, and R3 denote columns of the six-dimensional rotation matrix R.

15. The robot-assisted automatic introduction device for the trocar according to claim 14, wherein the introduction module is configured to acquire, according to the rotation matrix of the trocar, the orientation of the trocar, wherein the introduction module is configured to acquire a true value $$R_z^{pred}$$

of the trocar in the dataset, and calculate the orientation of the trocar according to the rotation matrix $$R_z^{gt}$$

of the trocar:

$$\Delta\theta = \text{across}(R_Z^{gt} \cdot R_Z^{pred});$$

wherein the orientation of the trocar is expressed by an angle Δθ between the rotation matrix $$R_z^{gt}$$

of the trocar and the true value $$R_z^{pred}$$

of the trocar.

* * * * *